(12) United States Patent
Goggins et al.

(10) Patent No.: US 7,879,542 B2
(45) Date of Patent: Feb. 1, 2011

(54) METHYLATED GENE BIOMARKERS FOR DETECTING CANCER

(75) Inventors: Michael G. Goggins, Baltimore, MD (US); Sato Norihiro, Fukuoka (JP)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/561,877

(22) Filed: Aug. 2, 2006

(65) Prior Publication Data

US 2007/0202499 A1 Aug. 30, 2007

Related U.S. Application Data

(63) Continuation of application No. PCT/US2004/020535, filed on Jun. 24, 2004.

(60) Provisional application No. 60/482,146, filed on Jun. 24, 2003.

(51) Int. Cl.
*C12Q 1/68* (2006.01)
*C07H 21/00* (2006.01)
*C07H 21/02* (2006.01)
*C07H 21/04* (2006.01)

(52) U.S. Cl. .......... 435/6; 536/22.1; 536/23.1; 536/24.3

(58) Field of Classification Search .......... 435/6, 435/91.2; 536/23.1, 243
See application file for complete search history.

(56) References Cited

U.S. PATENT DOCUMENTS

| | | | |
|---|---|---|---|
| 5,786,146 A | | 7/1998 | Herman et al. |
| 2002/0183501 A1* | | 12/2002 | Polyak et al. .............. 536/23.1 |
| 2003/0087258 A1* | | 5/2003 | Shuber ......................... 435/6 |
| 2003/0190616 A1* | | 10/2003 | Goggins et al. ................ 435/6 |
| 2005/0069924 A1 | | 3/2005 | Goggins et al. |
| 2005/0095611 A1 | | 5/2005 | Chan et al. |
| 2007/0015156 A1* | | 1/2007 | Goggins ........................ 435/6 |

FOREIGN PATENT DOCUMENTS

| | | | |
|---|---|---|---|
| WO | WO-00/72679 A1 | | 12/2000 |
| WO | PCT/US02/068694 | | 9/2002 |
| WO | WO-2004/083399 A2 | | 9/2004 |

OTHER PUBLICATIONS

Sato et al., SPARC/osteonectin is a frequent target for aberrant methylation in pancreatic adenocarcinoma and a mediator of tumor-stromal interactions. Oncogene 22(32) : 5021-5030 (2003).*

Jones et al., The Fundamental role of epigenetic events in cancer. Nature Reviews Genetics 3 : 415-428 (2002).*
Matsubayashi et al., Methylation of Cyclin D2 is observed frequently in pancreatic cancer but is also an age-related phenomenom in gasterintestinal tissues.Clinical Cancer Research 9 : 1446-1452 (Apr. 2003).*
Sato et al., SPARC/osteonectin is a frequent target for aberrant methylation in pancreatic adenocarcinoma and a mediator of tumor-stromal interactions. Oncogene 22 : 5021-5030 (2003).*
Sato et al., Discovery of novel targets for aberrant methylation in pancreatic carcinoma using high-throughput microarrays. Cancer Research 63 : 3735-3742 (2003).*
Ueki et al., Hypermethylation of Multiple Genes in Pancreatic Adenocarcinoma. Cancer Research 60 : 1835-1839 (2000).*
Geolz et al.,Hypomethylation of DNA from Benign and Malignant Human Colon Neoplasms. Science 228 (4696) : 187-190 (1985).*
Baylin et al. Alterations in DNA methylation : A Fundamental aspect of Neoplasia. Advances in Cancer Research 72 : 141-196 (1998).*
Jansen et al., Aberrant methylation of the 5' CpG island of TSLC1 is common in pancreatic ductal adenocarcinoma and is first manifest in high-grade PanINs. Cell Biology & Therapy 1(3) : 293-296 (2002).*
Sato et al. Aberrant Methylation of CpG islands in intraductalpapillary mucinous neoplasms of the pancreas. Gastroenterology 123: 365-372 (2002).*
Schutte et al., Abrogation of the Rb/p16 tumor-suppressive pathway in virtually all pancreatic carcinomas . Cancer Research 57 : 3126-3130 (1997).*
Sato Norihiro et al. "SPARC/osteonectin is a frequent target for aberrant methylation in pancreatic adenocarcinoma and a potential mediator of tumor-stromal interactions" Proceedings of the Annual Meeting of the American Association for Cancer Research, New York, NY, vol. 44, Jul. 14, 2003.
Sato Norihiro et al. "SPARC/osteonectin is a frequent target for aberrant methylation in pancreatic adenocarcinoma and a mediator of tumor-stromal interactions" Oncogene. Aug. 7, 2003, vol. 22, No. 32, XP002394202.
Hennessy Bryan T et al. "DNA Methylation in haematological malignancies: the role of decitabine," Expert Opinion on Investigational Drugs. Dec. 2003, vol. 12, No. 12, XP002394206.
Hafner et al., "A purine-rich sequence in the human BM-40 gene promoter region is a prerequisuisite for maximum transcription," Matrix Biology, Elsevier, vol. 14, No. 9, Dec. 9, 2005, XP005161976.
Database Genbank NCBI; Jul. 7, 2002 Hafner, M. et al., "*H. sapiens* BM-40 gene," XP002394219.
Ulbrecht, M, Supplementary Partial European Search Report for International Application PCT/US20004020535, Sep. 5, 2006.

* cited by examiner

*Primary Examiner*—Ethan Whisenant
(74) *Attorney, Agent, or Firm*—Edwards Angell Palmer & Dodge LLP; Peter F. Corless; Melissa Hunter-Ensor, Esq.

(57) ABSTRACT

The present invention includes methods diagnosising of cancer by analysis of a patient sample, particularly for the presence of a methylated SPARC nucleic acid molecule, and particularly for the diagnosis of pancreatic cancer. The invention also includes therapeutic methods for treating cancers by administering to cancers patients therapeutically effective amounts of demethylating agents.

16 Claims, 9 Drawing Sheets

H.sapiens BM-40 gene.
ACCESSION    X82259
VERSION      X82259.1  GI:1009408
KEYWORDS     retrotransposon; SPARC protein.

```
   1 gaattccttg tactttttt ccctctcag ttctgcactt aactcgtcta aaaaaattaa
  61 aaaagaattt aagaaaccac aaagctaagc tgggtgcggt ggctcacgcc tgtaatccta
 121 gcactttggg aagccaaggc attcggattg cccaagctca ggagttcgag accagcctgg
 181 gcaacatgtt gaaacccat ttctactaaa aatacaataa attagctggg tgttgtggca
 241 tgtgcgcctg taatcccagc tactctggag gctgaggcgc gataattgct tgaacccggg
 301 aggcagaggt tgcagtgagc cgaaatcata ccactgcact ccagcctggg cgacagagtg
 361 agtgagactc tgtctcaaaa caaaacaaaa caaacaaaca aaaaaccgg aaccaacaa
 421 aacttttga ggaacaaagg gaaccaggta ttttattaat tctcatacct ccagagtgtt
 481 aggcacaaaa taaacattca accaagacct gttgactga gcagttcata tataacagga
 541 gtgacccaag ttgaaacgta gaatcagccc tctcatacca cttttttgcca ggtgatcata
 601 ggcaagttac ttagcatcta tgtttcctta ttattaaaat ggtcataatt acaatgccta
 661 agataagggg gttgctgtga agattattaa atcctcagta aactttggct attgttactc
 721 ctatgattat catcaatatc atcaattacc ttatctgttc aatactggtg gcacaggtcc
 781 accagctaga tgtctaatcc cttatgtgtc tattagtggt acaagtggag tttgagtggg
 841 attttttttt ttttttttaa gaccagttcc aaatcatcaa ggatgatacc actagtagca
 901 gcttgtcttg tctgtacagt ggtaagtcct ggccttgcct ttgtggcaaa tacaacccc
 961 ttgaattgct tggcccttct cagcattgcc taatattagg gaggactcct gtaaagctca
1021 ctggttagaa gatcaagaca cttgggcctg gttctgcccc tgggggccat tgggtaattc
1081 cttaagtct ccaggcctca cttgccctct gaacaagaaa gaggcctgtt ctggtcatcc
1141 ctccagcctg tccagccctg gcactctgtg agtcggttta ggcagcagcc ccggaacaga
1201 tgaggcaggc agggttggga cgtttggtca ggacagccca ccgcaaaaag aggaggaaag
1261 aaatgaaaga cagagacagc tttggctatg ggagaaggag gaggccgggg gaaggaggag
1321 acaggaggag gagggaccac ggggtggagg ggagatagac ccagcccaga gctctgagtg
1381 gtttcctgtt gcctgtctc ▓▓▓▓▓▓▓▓▓▓▓▓▓▓▓▓▓▓▓▓▓▓▓▓▓▓▓▓▓▓▓▓▓▓▓▓▓▓▓▓
     ▓▓▓▓▓▓▓▓▓▓▓▓▓▓▓▓▓▓▓▓▓▓▓▓▓▓▓▓▓▓▓▓▓▓▓▓▓▓g tatgtgtgac cccgcccag
1501 ccttttcctt ctatagttgc accaaccocg acaccccgt tcacgccgtc agctcgtgtg
1561 caagggaggg aagctctgct gaggatgcgc ctctcctccc ggctccatca cggctcccct
```

Figure 6

```
1621 taagagcatg gccctcggtc ctgtctgcct gttgcttttc agaaggtgga ctcactgtgt
1681 aactttgtct tcccttacag gtttacagga aaataatctc actatgttct tcgggggagc
1741 attttctcac tctctgtttt tctctgtgtc tgtctctggt ttcagaggct gcctgcctgt
1801 cctctttgct ccctttgcaa atgtggcagc ctcctccttt cctgggaatc tgatcccatc
1861 acagctgcca cagggacctg gccagcaacc ggagtctgtc ctccagatct cggtcagggg
1921 ttctgttttc caaaaaggga ctttgcagaa caatcagttg atctctgaaa gggaaagggg
1981 gaggcttcac cattaatcca caccctgggg aagcttctgt tttcctctaa ttctcctcac
2041 tcccaaacac caccttccgt cccccaata cacaaatttc agcaccattc tgcctgaaat
2101 ggcaccatca caacctcagt cttgggttag gtgttgttcc tgtcctgagt tccttgggat
2161 ggtaaacaca ggcagtagcc cttagtttat ctagatctga aaacccagac atcagatatc
2221 gtcaaccaag acatgggtgt aatgggaggt ggagtgtgct gggggagata ttctcagaag
2281 ggggaaaggg ggaagggaag agggagagaa ttc
```

Figure 6 (continued)

Bisulfite Sequencing primers forward; ATT TAG TTT AGA GTT TTG AGT GG (position 1359-1381)
reverse; ACA AAA CTT CCC TCC CTT AC (position 1560-1579)

```
1081 tttssagttt ttaggtttta tttgttttt gaataagaaa gaggtttgtt ttggttattt
1141 ttttagtttg tttagttttg gtattttgtg agtcggttta ggtagtagtt tcggaataga
1201 tgaggtaggt agggttggga cgtttggtta ggatagttta tcgtaaaaag aggaggaaag
1261 aaatgaaaga tagagatagt tttggttatg ggagaaggag gaggtcgggg gaaggaggag
1321 ataggaggag gagggattac ggggtggagg ggagatag
1381 ttttttgtt gttgttttt aatttttt atattttcgc ggtttttag attgttcgga
1441 gagcgcgttt tgtttgtcgt ttgtttgttt gttattgagg tatgtgtgat tttcgtttag
1501 ttttttttt ttatagttgt attaatttcg atattttcgt ttacgtcgtt agttcgtgt
1561                        t gaggatgcgt ttttttttc ggttttatta cggttttttt
1621 taagagtatg gttttcggtt ttgtttgttt gttgttttt agaaggtgga tttattgtgt
1681 aattttgttt tttttatag gtttatagga aataattttt attatgtttt tcgggggagt
1741 atttttttat tttttgtttt ttttgtgtt tgttttggt tttagaggtt gtttgtttgt
1801 ttttttgtt tttttgtaa atgtggtagt ttttttttt tttgggaatt tgattttatt
1861 atagttgtta tagggatttg gttagtaatc ggagtttgtt tttagatttt cggttagggg
1921 ttttgttttt taaaaggga ttttgtagaa taattagttg atttttgaaa gggaaaggg
1981 gaggttttat tattaattta tattttggg aagttttgt tttttttaa tttttttat
2041 ttttaaatat tattttcgt tttttaata tataaatttt agtattattt tgtttgaaat
```

Figure 7

Methylation specific PCR primers

Unmethylated forward; TTT TTT AGA TTG TTT GGA GAG TG (position 1423-1445)
Reverse; AAC TAA CAA CAT AAA CAA AAA TAT C (position 1530-1554)

```
1321 ataggaggag gagggattat ggggtggagg ggagatagat ttagtttaga gttttgagtg
1381 gttttttgtt gtttgttttt aatttttttt atatttttgt gg................
1441 ......tgttt tgtttgttgt ttgtttgttt gttattgagg tatgtgtgat ttttgtttag
1501 tttttttttt ttatagttgt attaatttt.......................tgtgtg
1561 taagggaggg aagttttgtt gaggatgtgt tttttttttt ggttttatta tggttttttt
1621 taagagtatg gttttggtt ttgtttgttt gttgttttttt agaaggtgga tttattgtgt
```

Figure 8A

Methylated forward; GAG AGC GCG TTT TGT TTG TC (position 1439-1458)
Reverse; AAC GAC GTA AAC GAA AAT ATC G (position 1529-1550)

```
1321 ataggaggag gagggattac ggggtggagg ggagatagat ttagtttaga gttttgagtg
1381 gttttttgtt gtttgttttt aatttttttt atatttttcgc ggttttttag attgttcg..
1441 ..................gt ttgtttgttt gttattgagg tatgtgtgat tttcgtttag
1501 tttttttttt ttatagttgt attaatttt..................... agttcgtgtg
1561 taagggaggg aagttttgtt gaggatgcgt ttttttttc ggttttatta cggttttttt
1621 taagagtatg gtttttcggtt ttgtttgttt gttgttttttt agaaggtgga tttattgtgt
```

Figure 8B

METHYLATED GENE BIOMARKERS FOR DETECTING CANCER

The provisional application U.S. Ser. No. 60/482,146 filed Jun. 24, 2003 is incorporated herein, by reference, in its entirety.

FIELD OF THE INVENTION

The invention provides for methylated gene biomarkers important in the detection of cancer. More particularly, the present invention relates to a biomarker which is a methylated gene for SPARC.

BACKGROUND OF THE INVENTION

Several publications and patent documents are cited throughout the specification in order to describe the state of the art to which this invention pertains. Full citations for those references that are numbered can be found at the end of the specification. Each citation is incorporated herein as though set forth in full.

Pancreatic cancer continues to have one of the highest mortality rates of any malignancy. Each year, 28,000 patients are diagnosed with pancreatic cancer, and most will die of the disease. The vast majority of patients are diagnosed at an advanced stage of disease because currently no tumor markers are known that allow reliable screening for pancreas cancer at an earlier, potentially curative stage. This is a particular problem for those patients with a strong familial history of pancreatic cancer, who may have up to a 5-7 fold greater risk of developing pancreatic cancer in their lifetime. Despite several advances in our basic understanding and clinical management of pancreatic cancer, virtually all patients who will be diagnosed with pancreatic cancer will die from this disease. The high mortality of pancreatic cancer is predominantly due to consistent diagnosis at an advanced stage of disease, and a lack of effective screening methods.

Infiltrating ductal adenocarcinoma of the pancreas is one of the most aggressive of all of the solid neoplasms, and invasive pancreatic cancer is often associated with a prominent host desmoplastic response. Besides the potential aggressiveness of neoplastic cells themselves, this host response at the site of primary invasion has been considered an important factor in pancreatic cancer progression. Indeed, evidence exists for interactions between pancreatic cancer cells and stromal fibroblasts that affect the invasive phenotype of pancreatic cancer (Maehara et al., 2001). In contrast to the substantial progress in our understanding of the genetic and epigenetic events that occur within pancreatic cancer cells, molecular mechanisms associated with the tumor-host interactions have not been well characterized. Ryu and colleagues used serial analysis of gene expression (SAGE) to compare gene expression profiles of primary carcinomas and passaged cancer cell lines, and identified a cluster of invasion-specific genes (Ryu et al., 2001). Many of the genes identified were expressed specifically by stromal cells adjacent to the neoplastic epithelium, thus representing potential mediators of the tumor-host interactions (Iacobuzio-Donahue et al., 2002b).

SPARC (secreted protein acidic and rich in cysteine)/osteonectin/BM 40 is a matricellular glycoprotein involved in diverse biological processes, including tissue remodeling, wound repair, morphogenesis, cellular differentiation, cell proliferation; cell migration, and angiogenesis (Jendraschak and Sage, 1996; Yan and Sage, 1999; Bradshaw and Sage, 2001; Brekken and Sage, 2001). SPARC is highly expressed in a wide range of human malignant neoplasms, and the deregulated expression of SPARC is often correlated with disease progression and/or poor prognosis (Wewer et al., 1988; Bellahcene and Castronovo, 1995; Porte et al., 1995; Porter et al., 1995; Ledda et al., 1997; Porte et al., 1998; Massi et al., 1999; Rempel et al., 1999; Thomas et al., 2000; Yamanaka et al., 2001). Interestingly, in certain tumor types, strong expression of SPARC has been detected predominantly in the stroma adjacent to the neoplastic cells (Le Bail et al., 1999; Paley et al., 2000; Iacobuzio-Donahue et al., 2002a). These findings have led to the hypothesis that SPARC plays a role in tumor progression at the site of interface between neoplastic cells and the surrounding host cells. Recently, Yiu and coworkers have shown that treatment of ovarian cancer cells with exogenous SPARC inhibits cell proliferation and induces apoptosis (Yiu et al., 2001). In addition, forced expression of SPARC in ovarian cancer cells resulted in reduced tumorigenicity in nude mice, suggesting that SPARC has a tumor-suppressor function (Mok et al., 1996). In addition to its effects on cellular proliferation, SPARC has been linked with tumor invasion. SPARC has been shown to increase the invasive capacity of prostate and breast cancer cells in vitro (Jacob et al., 1999; Briggs et al., 2002) and promote invasion of glioma in vivo (Schultz et al., 2002). Thus, the biological functions of SPARC appear to be variable among cancer types, and it is not known whether this protein is involved in pancreatic cancer progression.

There is an urgent need, therefore, to determine SPARC's exact role in pancreatic cancer and other types of cancer. Furthermore, there is also a great need for the development of new methods for detection and diagnosis of pancreatic cancers, particularly at a pre-invasive or early stage of the disease so that early medical intervention can be more effective at saving lives. Indeed, new methods of detection for pancreatic cancer may be useful in diagnosing other types of cancer, as well.

SUMMARY OF THE INVENTION

The invention provides methods for the detection of cancer, in particular pancreatic cancer, at an early stage of the disease that can allow for early medical treatment and enhanced patient survival rates.

The present invention relates to methods for diagnosing cancer, comprising the detection of a methylated SPARC nucleic acid molecule or a variant thereof in a sample from a subject. The method of the invention includes modification of SPARC DNA by sodium bisulfite or a comparable agent which converts all unmethylated but not methylated cytosines to uracil, and subsequent amplification with primers specific for methylated versus unmethylated DNA. This method of "methylation specific PCR" or MSP, requires only small amounts of DNA, is sensitive to 0.1% of methylated alleles of a given CpG island locus, and can be preformed from a variety of sample types.

The presence of the methylated SPARC nucleic acid molecules is correlated to a sample of a normal subject. The sample is preferably obtained from a mammal suspected of having a proliferative cell growth disorder, in particular, a pancreatic cancer.

In a preferred embodiment a nucleic acid molecule that is indicative of a pancreatic cancer comprises a sequence having at least about 80% sequence identity to a molecule identified in SEQ ID NO: 1 (SPARC nucleic acid sequence), more preferably the nucleic acid molecule comprises a sequence having at least about 90% sequence identity to a molecule identified in SEQ ID NO: 1, most preferably the nucleic acid molecule comprises a sequence having at least about 95% sequence identity to a molecule identified in SEQ ID NO: 1.

In another preferred embodiment, the nucleic acid molecule is expressed at a lower level in a patient with cancer as compared to expression levels in a normal individual. Preferably the nucleic acid molecule is expressed at least about 15 fold lower in a patient with cancer as compared to expression in a normal individual, more preferably the nucleic acid molecule is expressed at least about 10 fold lower in a patient with cancer as compared to expression in a normal individual, most preferably the nucleic acid molecule is expressed at least about 5 fold lower in a patient with cancer as compared to expression in a normal individual.

In another preferred embodiment, the sample used for detection of preferred nucleic acid molecules is obtained from a mammalian patient, including a human patient.

The invention also provides methods for treating a mammal suffering from cancer comprising administering to the mammal a therapeutically effective amount of a demethylating agent. The method can be used to treat a patient is suffering from a pancreatic cancer.

Diagnostic kits are also provided comprising a molecule substantially complementary to a sequence corresponding to a molecule identified in SEQ ID NO: 1. Preferably, the kit comprises a molecule comprising a sequence having at least about 80% sequence identity to a molecule identified in SEQ ID NO: 1, more preferable at least about 90% sequence identity to a molecule identified in SEQ ID NO: 1, most preferable the kit comprises a molecule comprising a sequence having at least about 95% sequence identity to a molecule identified in SEQ ID NO: 1.

Preferably, the kit comprises written instructions for use of the kit for detection of cancer and the instructions provide for detecting methylated SPARC nucleic acid molecules from cancer patients.

Other aspects of the invention are described infra.

BRIEF DESCRIPTION OF THE FIGURES

FIG. 6 represents the nucleic acid sequence for the human SPARC gene (SEQ ID NO: 1); Accession Number X82259.

FIG. 7 represents the nucleic acid sequence (SEQ ID NO: 8) for the bisulfite sequencing primers; forward (SEQ ID NO: 2) and reverse (SEQ ID NO: 3).

FIG. 8 represents the methylation specific PCR primers: Unmethylated (DNA sequence disclosed as SEQ ID NO: 9), forward (SEQ ID NO: 4) and reverse (SEQ ID NO: 5); and Methylated (DNA sequence disclosed as SEQ ID NO: 10), forward (SEQ ID NO: 6) and reverse (SEQ ID NO: 7).

DETAILED DESCRIPTION OF THE INVENTION

Figure 1:
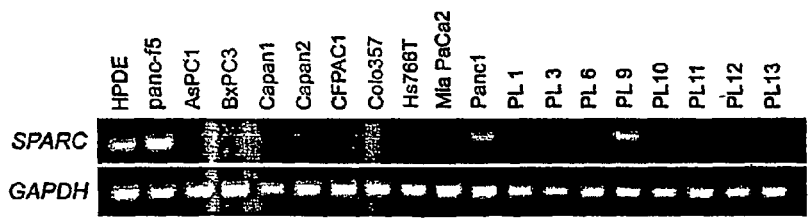
FIG. 1 represents (a) Online SAGE Tag to Gene Mapping analysis demonstrating the frequency of the Hs.111779 tag (ATGTGAAGAG (SEQ ID NO: 13)) corresponding to the SPARC gene in 8 pancreatic SAGE libraries derived from short-term cultures of normal pancreatic ductal epithelial cells (H126 and HX), pancreatic cancer cell lines (CAPAN1, CAPAN2, HS766T, and Panc1), and primary pancreatic adenocarcinoma tissue (Panc 91-16113 and Panc 96-6252); (b) Gene expression analysis of SPARC by oligonucleotide microarrays in two frozen tissue samples of normal pancreatic ductal epithelial cells selectively microdissected by LCM, a non-neoplastic pancreatic epithelial cell line (HPDE), and 5 pancreatic cancer cell lines (AsPC1, CFPAC1, Hs766T, MiaPaCa2, and Panc1); (c) Reverse transcription-PCR analysis of SPARC in a non-neoplastic pancreatic duct epithelial cell line (HPDE), primary fibroblasts derived from pancreatic cancer, and 17 pancreatic cancer cell lines; glyceraldehyde-3-phosphate dehydrogenase (GAPDH) serves as an RNA control.

It is understood that this invention is not limited to the particular materials and methods described herein. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"Biomarker" in the context of the present invention refers to a nucleic acid molecule which is present in a sample taken from patients having human cancer as compared to a comparable sample taken from control subjects (e.g., a person with a negative diagnosis or undetectable cancer, normal or healthy subject). In the context of the present invention, the biomarker is specifically methylated SPARC, as identified in SEQ ID NO: 1 or a variant thereof.

"Diagnostic" means identifying the presence or nature of a pathologic condition. In the context of the present invention with regard to cancer, the presense of a methylated SPARC nucleic acid is diagnostic of cancer, and in particular pancreatic cancer, Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., µg/ml) or a relative amount (e.g., relative intensity of signals).

A "diagnostic amount" of a marker refers to an amount of a marker in a subject's sample that is consistent with a diagnosis of human cancer. A diagnostic amount can be either in absolute amount (e.g., µg/ml) or a relative amount (e.g., relative intensity of signals).

A "control amount" of a marker can be any amount or a range of amount which is to be compared against a test amount of a marker. For example, a control amount of a marker can be the amount of a marker in a person without human cancer. A control amount can be either in absolute amount (e.g., µg/ml) or a relative amount (e.g., relative intensity of signals).

"Detect" refers to identifying the presence, absence or amount of the object to be detected.

By "patient" herein is meant a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, "proliferative growth disorder, "neoplastic disease," "tumor; "cancer" are used interchangeably as used herein refers to a condition characterized by uncontrolled, abnormal growth of cells. Preferably the cancer to be treated is pancreatic cancer and the abnormal proliferation of cells in the pancreas can be any cell in the organ. Examples of cancer include but are not limited to, carcinoma, blastoma, and sarcoma. As used herein, the term "carcinoma" refers to a new growth that arises from epithelium, found in skin or, more commonly, the lining of body organs.

The term "in need of such treatment" as used herein refers to a judgment made by a care giver such as a physician, nurse, or nurse practitioner in the case of humans that a patient requires or would benefit from treatment. This judgment is made based on a variety of factors that are in the realm of a care giver's expertise, but that include the knowledge that the patient is ill, or will be ill, as the result of a condition that is treatable by the compounds of the invention.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

An "effective amount" of a composition disclosed herein or an agonist thereof, in reference to "inhibiting the cellular proliferation" of a neoplastic cell, is an amount capable of inhibiting, to some extent, the growth of target cells. The term further includes an amount capable of involing a growth inhibitory, cytostatic and/or cytotoxic effect and/or apoptosis and/or necrosis of the target cells. An "effective amount" of, for example a potential candidate agent that interacts with the nucleic acid molecules described herein, for purposes of inhibiting neoplastic cell growth may be determined empirically and in a routine manner using methods well known in the art.

A "therapeutically effective amount", in reference to the treatment of neoplastic disease or neoplastic cells, refers to an amount capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder.

In another aspect, the invention provides methods for detecting biomarkers (i.e., methylated SPARC) which are present in the samples of a human cancer patient and a control (e.g., an individual in whom human cancer is undetectable). The biomarkers can be detected in a number of biological samples. The sample is preferably a biological fluid, tissue or organ sample. Examples of a biological fluid sample useful in this invention include blood, blood serum, plasma, pancreatic fluids, aspirate, urine, tears, saliva, etc.

Detection of SPARC Nucleic Acid Molecules

The normal pancreas contains a predominance of acinar cells and islets relative to normal duct epithelium. The normal pancreatic duct epithelium is therefore underrepresented in gene expression analyses of bulk normal pancreas. Therefore, in a preferred embodiment, the SPARC gene identified by a biochip, such as for example, Affymetrix GeneChip, are further refined to exclude genes highly expressed in cultures of normal pancreatic ductal epithelial cells. For each gene identified as differentially expressed by Affymetrix GeneChip, the corresponding SAGE tag was identified, and the total number of SAGE tags present in the SAGEmap database (http://www.ncbi.nlm.nih.gov/SAGE/) of normal pancreas duct epithelium libraries HX and H126 was determined. Preferably, any gene having at least about five tags in about one of these two SAGE libraries was then excluded from further analysis.

Serial Analysis of Gene Expression (SAGE), is based on the identification of and characterization of partial, defined sequences of transcripts corresponding to gene segments. These defined transcript sequence "tags" are markers for genes which are expressed in a cell, a tissue, or an extract, for example.

SAGE is based on several principles. First, a short nucleotide sequence tag (9 to 10 bp) contains sufficient information content to uniquely identify a transcript provided it is isolated from a defined position within the transcript. For example, a sequence as short as 9 bp can distinguish 262,144 transcripts (4.sup.9) given a random nucleotide distribution at the tag site, whereas estimates suggest that the human genome encodes about 80,000 to 200,000 transcripts (Fields, et al., Nature Genetics, 7:345 1994). The size of the tag can be shorter for lower eukaryotes or prokaryotes, for example, where the number of transcripts encoded by the genome is lower. For example, a tag as short as 6-7 bp may be sufficient for distinguishing transcripts in yeast.

Second, random dimerization of tags allows a procedure for reducing bias (caused by amplification and/or cloning). Third, concatenation of these short sequence tags allows the efficient analysis of transcripts in a serial manner by sequencing multiple tags within a single vector or clone. As with serial communication by computers, wherein information is transmitted as a continuous string of data, serial analysis of the sequence tags requires a means to establish the register and boundaries of each tag. The concept of deriving a defined tag from a sequence in accordance with the present invention is useful in matching tags of samples to a sequence database. In the preferred embodiment, a computer method is used to match a sample sequence with known sequences.

The tags used herein, uniquely identify genes. This is due to their length, and their specific location (3') in a gene from which they are drawn. The full length genes can be identified by matching the tag to a gene data base member, or by using the tag sequences as probes to physically isolate previously unidentified genes from cDNA libraries. The methods by which genes are isolated from libraries using DNA probes are well known in the art. See, for example, Veculescu et al., Science 270: 484 (1995), and Sambrook et al. (1989), MOLECULAR CLONING: A LABORATORY MANUAL, 2nd ed. (Cold Spring Harbor Press, Cold Spring Harbor, N.Y.). Once a gene or transcript has been identified, either by matching to a data base entry, or by physically hybridizing to a cDNA molecule, the position of the hybridizing or matching region in the transcript can be determined. If the tag sequence is not in the 3' end, immediately adjacent to the restriction enzyme used to generate the SAGE tags, then a spurious match may have been made. Confirmation of the identity of a SAGE tag can be made by comparing transcription levels of the tag to that of the identified gene in certain cell types.

Analysis of gene expression is not limited to the above method but can include any method known in the art. All of these principles may be applied independently, in combination, or in combination with other known methods of sequence identification.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutchiffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF)(Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (reviewed in (To, Comb. Chem. High Throughput Screen, 2000, 3, 235-41).

In a preferred embodiment, Expressed Sequenced Tags (ESTs), can also be used to identify nucleic acid molecules which are over expressed in a cancer cell. ESTs from a variety of databases can be indentified. For example, preferred databases include, for example, Online Mendelian Inheritance in Man (OMIM), the Cancer Genome Anatomy Project (CGAP), GenBank, EMBL, PIR, SWISS-PROT, and the like. OMIM, which is a database of genetic mutations associated with disease, was developed, in part, for the National Center for Biotechnology Information (NCBI). OMIM can be accessed through the world wide web of the Internet, at, for example, ncbi.nlm.nih.gov/Omim/. CGAP, which is an interdisciplinary program to establish the information and technological tools required to decipher the molecular anatomy of a cancer cell. CGAP can be accessed through the world wide web of the Internet, at, for example, ncbi.nlm.nih.gov/ncic-gap/. Some of these databases may contain complete or partial nucleotide sequences. In addition, alternative transcript forms can also be selected from private genetic databases. Alternatively, nucleic acid molecules can be selected from available publications or can be determined especially for use in connection with the present invention.

Alternative transcript forms can be generated from individual ESTs which are within each of the databases by computer software which generates contiguous sequences. In another embodiment of the present invention, the nucleotide sequence of the nucleic acid molecule is determined by assembling a plurality of overlapping ESTs. The EST database (dbEST), which is known and available to those skilled in the art, comprises approximately one million different human mRNA sequences comprising from about 500 to 1000 nucleotides, and various numbers of ESTs from a number of different organisms. dbEST can be accessed through the world wide web of the Internet, at, for example, ncbi.nlm.nih.gov/dbEST/index.html. These sequences are derived from a cloning strategy that uses cDNA expression clones for genome sequencing. ESTs have applications in the discovery of new genes, mapping of genomes, and identification of coding regions in genomic sequences. Another important feature of EST sequence information that is becoming rapidly available is tissue-specific gene expression data. This can be extremely useful in targeting selective gene(s) for therapeutic intervention. Since EST sequences are relatively short, they must be assembled in order to provide a complete sequence. Because every available clone is sequenced, it results in a number of overlapping regions being reported in the database. The end result is the elicitation of alternative transcript forms from, for example, normal cells and cancer cells.

Assembly of overlapping ESTs extended along both the 5' and 3' directions results in a full-length "virtual transcript." The resultant virtual transcript may represent an already characterized nucleic acid or may be a novel nucleic acid with no known biological function. The Institute for Genomic Research (TIGR) Human Genome Index (HGI) database, which is known and available to those skilled in the art, contains a list of human transcripts. TIGR can be accessed through the world wide web of the Internet, at, for example, tigr.org. Transcripts can be generated in this manner using TIGR-Assembler, an engine to build virtual transcripts and which is known and available to those skilled in the art. TIGR-Assembler is a tool for assembling large sets of overlapping sequence data such as ESTs, BACs, or small genomes, and can be used to assemble eukaryotic or prokaryotic sequences. TIGR-Assembler is described in, for example, Sutton, et al., Genome Science & Tech., 1995, 1, 9-19, which is incorporated herein by reference in its entirety, and can be accessed through the file transfer program of the Internet, at, for example, tigr.org/pub/software/TIGR. assembler. In addition, GLAXO-MRC, which is known and available to those skilled in the art, is another protocol for constructing virtual transcripts. In addition, "Find Neighbors and Assemble EST Blast" protocol, which runs on a UNIX platform, has been developed by Applicants to construct virtual transcripts. PHRAP is used for sequence assembly within Find Neighbors and Assemble EST Blast. PHRAP can be accessed through the world wide web of the Internet, at, for example, chimera.biotech.washington.edu/uwgc/tools/phrap.htm. Identification of ESTs and generation of contiguous ESTs to form full length RNA molecules is described in detail in U.S. application Ser. No. 09/076,440, which is incorporated herein by reference in its entirety.

In yet another aspect, variants of the nucleic acid molecules as identified in FIGS. 1A through 1M can be used to detect pancreatic cancers. An "allele" or "variant" is an alternative form of a gene. Of particular utility in the invention are variants of the genes encoding any potential pancreatic tumor markers identified by the methods of this invention. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

To further identify variant nucleic acid molecules which can detect, for example, pancreatic cancer at an early stage, nucleic acid molecules can be grouped into sets depending on the homology, for example. The members of a set of nucleic acid molecules are compared. Preferably, the set of nucleic acid molecules is a set of alternative transcript forms of nucleic acid. Preferably, the members of the set of alternative transcript forms of nucleic acids include at least one member which is associated, or whose encoded protein is associated, with a disease state or biological condition. Thus, comparison of the members of the set of nucleic acid molecules results in the identification of at least one alternative transcript form of nucleic acid molecule which is associated, or whose encoded protein is associated, with a disease state or biological condition. In a preferred embodiment of the invention, the members of the set of nucleic acid molecules are from a common gene. In another embodiment of the invention, the members of the set of nucleic acid molecules are from a plurality of genes. In another embodiment of the invention, the members of the set of nucleic acid molecules are from different taxonomic species. Nucleotide sequences of a plurality of nucleic acids from different taxonomic species can be identified by performing a sequence similarity search, an ortholog search, or both, such searches being known to persons of ordinary skill in the art.

Sequence similarity searches can be performed manually or by using several available computer programs known to those skilled in the art. Preferably, Blast and Smith-Waterman algorithms, which are available and known to those skilled in the art, and the like can be used. Blast is NCBI's sequence similarity search tool designed to support analysis of nucleotide and protein sequence databases. Blast can be accessed through the world wide web of the Internet, at, for example, ncbi.nln.nih.gov/BLAST/. The GCG Package provides a local version of Blast that can be used either with public domain databases or with any locally available searchable database. GCG Package v9.0 is a commercially available software package that contains over 100 interrelated software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG can be accessed through the Internet at, for example, http://www.gcg.com/. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for homology searching, gene finding, multiple sequence alignment, secondary structure prediction, and motif identification. GeneThesaurus 1.0 tm is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and parses all the GenBank fields into "tab-delimited" text that can then be saved in a "relational database" format for easier search and analysis, which provides flexibility. The end result is a series of completely parsed GenBank records that can be easily sorted, filtered, and queried against, as well as an annotations-relational database.

Preferably, the plurality of nucleic acids from different taxonomic species which have homology to the target nucleic acid, as described above in the sequence similarity search, are further delineated so as to find orthologs of the target nucleic acid therein. An ortholog is a term defined in gene classification to refer to two genes in widely divergent organisms that have sequence similarity, and perform similar functions within the context of the organism. In contrast, paralogs are genes within a species that occur due to gene duplication, but have evolved new functions, and are also referred to as isotypes. Optionally, paralog searches can also be performed. By performing an ortholog search, an exhaustive list of homologous sequences from as diverse organisms as possible is obtained. Subsequently, these sequences are analyzed to select the best representative sequence that fits the criteria for being an ortholog. An ortholog search can be performed by programs available to those skilled in the art including, for example, Compare. Preferably, an ortholog search is performed with access to complete and parsed GenBank annotations for each of the sequences. Currently, the records obtained from GenBank are "flat-files", and are not ideally suited for automated analysis. Preferably, the ortholog search is performed using a Q-Compare program. Preferred steps of the Q-Compare protocol are described in the flowchart set forth in U.S. Pat. No. 6,221,587, incorporated herein by reference.

Preferably, interspecies sequence comparison is performed using Compare, which is available and known to those skilled in the art. Compare is a GCG tool that allows pair-wise comparisons of sequences using a window/stringency criterion. Compare produces an output file containing points where matches of specified quality are found. These can be plotted with another GCG tool, DotPlot.

The SPARC nucleic acid molecules of this invention can be isolated using the technique described in the experimental section or replicated using PCR. The PCR technology is the subject matter of U.S. Pat. Nos. 4,683,195, 4,800,159, 4,754,065, and 4,683,202 and described in PCR: The Polymerase Chain Reaction (Mullis et al. eds, Birkhauser Press, Boston (1994)) or MacPherson et al. (1991) and (1994), supra, and references cited therein (see Methylation Specific PCR below). Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (procaryotic or eucaryotic) for replication and amplification. The DNA so amplified can be isolated from the cell by methods well known to those of skill in the art. A process for obtaining polynucleotides by this method is further provided herein as well as the polynucleotides so obtained.

The terms "nucleic acid molecule" and "tumor marker" or "polynucleotide" will be used interchangeably throughout the specification, unless otherwise specified. As used herein, "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

In an embodiment of the invention the presence of amethylated SPARC nucleic acid molecule is correlated to a sample of a normal subject. The sample is preferably obtained from a mammal suspected of having a proliferative cell growth disorder, in particular, a pancreatic cancer. Preferably, a nucleic acid molecule that is indicative of a cancer comprises a sequence having at least about 80% sequence identity to a molecule identified in SEQ ID NO: 1, more preferably the nucleic acid molecule comprises a sequence having at least about 90% sequence identity to a molecule identified in SEQ ID NO: 1, most preferably the nucleic acid molecule comprises a sequence having at least about 95% sequence identity to a molecule identified in SEQ ID NO: 1.

In another preferred embodiment, the nucleic acid molecule is expressed at a lower level in a patient with cancer as compared to expression levels in a normal individual. Preferably the nucleic acid molecule is expressed at least about 15 fold lower in a patient with cancer as compared to expression in a normal individual, more preferably the nucleic acid molecule is expressed at least about 10 fold lower in a patient with cancer as compared to expression in a normal individual, most preferably the nucleic acid molecule is expressed at least about 5 fold lower in a patient with cancer as compared to expression in a normal individual.

Percent identity and similarity between two sequences (nucleic acid or polypeptide) can be determined using a mathematical algorithm (see, e.g., *Computational Molecular Biology*, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

To determine the percent identity of two amino acid sequences or of two nucleic acid sequences, the sequences are aligned for optimal comparison purposes (e.g., gaps are introduced in one or both of a first and a second amino acid or nucleic acid sequence for optimal alignment and non-homologous sequences can be disregarded for comparison purposes). The percent identity between the two sequences is a function of the number of identical positions shared by the sequences, taking into account the number of gaps, and the length of each gap which need to be introduced for optimal alignment of the two sequences. The amino acid residues or nucleotides at corresponding amino acid positions or nucleotide positions, respectively, are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

A "comparison window" refers to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art.

For example, the percent identity between two amino acid sequences can be determined using the Needleman and Wunsch algorithm (J. Mol. Biol. (48): 444-453, 1970) which is part of the GAP program in the GCG software package (available at http://www.gcg.com), by the local homology algorithm of Smith & Waterman (Adv. Appl. Math. 2: 482, 1981), by the search for similarity methods of Pearson & Lipman (Proc. Natl. Acad. Sci. USA 85: 2444, 1988) and Altschul, et al. (Nucleic Acids Res. 25(17): 3389-3402, 1997), by computerized implementations of these algorithms (GAP, BESTFIT, FASTA, and BLAST in the Wisconsin Genetics Software Package (available from, Genetics Computer Group, 575 Science Dr., Madison, Wis.), or by manual alignment and visual inspection (see, e.g., Ausubel et al., supra). Gap parameters can be modified to suit a user's needs. For example, when employing the GCG software package, a NWSgapdna.CMP matrix and a gap weight of 40, 50, 60, 70, or 80 and a length weight of 1, 2, 3, 4, 5, or 6 can be used. Examplary gap weights using a Blossom 62 matrix or a PAM250 matrix, are 16, 14, 12, 10, 8, 6, or 4, while exemplary length weights are 1, 2, 3, 4, 5, or 6. The GCG software package can be used to determine percent identity between nucleic acid sequences. The percent identity between two amino acid or nucleotide sequences also can be determined using the algorithm of E. Myers and W. Miller (CABIOS 4: 11-17, 1989) which has been incorporated into the ALIGN program (version 2.0), using a PAM120 weight residue table, a gap length penalty of 12 and a gap penalty of 4.

The nucleic acid sequences of the present invention can further be used as query sequences to perform a search against sequence databases to, for example, identify other family members or related sequences. Such searches can be performed using the NBLAST and XBLAST programs (version 2.0) of Altschul, et al. (J. Mol. Biol. 215: 403-10, 1990). BLAST nucleotide searches can be performed with the NBLAST program, with exemplary scores=100, and wordlengths=12 to obtain nucleotide sequences homologous to or with sufficient percent identity to the nucleic acid molecules of the invention. BLAST protein searches can be performed with the XBLAST program, with exemplary scores=50 and wordlengths=3 to obtain amino acid sequences sufficiently homologous to or with sufficient % identity to the proteins of the invention. To obtain gapped alignments for comparison purposes, gapped BLAST can be used as described in Altschul et al. (Nucleic Acids Res. 25(17): 3389-3402, 1997). When using BLAST and gapped BLAST programs, the default parameters of the respective programs (e.g., XBLAST and NBLAST) can be used.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual Second Edition* (1989) Cold Spring Harbor Laboratory Press, Cold Spring Harbor, N.Y. (herein "Sambrook et al., 1989"); *DNA Cloning: A Practical Approach. Volumes I and II* (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

As used herein, the term "fragment or segment", as applied to a nucleic acid sequence, gene, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid fragments which begin at the amino terminal end of a nucleic acid and end at the carboxy terminal end of the nucleic acid or protein. Each nucleic acid or fragment has at least about one contiguous nucleic acid position in common with the next nucleic acid fragment, more preferably at least about three contiguous nucleic acid bases in common, most preferably at least about ten contiguous nucleic acid bases in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides. Additional preferred embodiments will include lengths in excess of those numbers, e.g., 63, 72, 87, 96, 105, 117, etc. Said fragments may have termini at any pairs of locations, but especially at boundaries between structural domains, e.g., membrane spanning portions.

Homologous nucleic acid sequences, when compared, exhibit significant sequence identity or similarity. The standards for homology in nucleic acids are either measures for homology generally used in the art by sequence comparison or based upon hybridization conditions. The hybridization conditions are described in greater detail below.

As used herein, "substantial homology" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually it least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a fragment derived from FIGS. 1A through 1M, e.g., 39829_at. Typically, selective hybridization will occur when there is at least about 55% homology over a stretch of at least about 14 nucleotides, preferably at least about 65%, more preferably at least about 75%, and most preferably at least about 90%. See, Kanehisa (1984) Nuc. Acids Res. 12:203-213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The endpoints of the segments may be at many different pair combinations.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) J. Mol. Biol. 31:349-370.

Methylation Specific Polymerase Chain Reaction (MSP)

In one embodiment, the invention provides a method for detecting a methylated CpG-containing SPARC nucleic acid, the method including contacting a nucleic acid-containing specimen with an agent that modifies unmethylated cytosine; amplifying the CpG-containing nucleic acid in the specimen by means of CpG-specific oligonucleotide primers; and detecting the methylated nucleic acid. It is understood that while the amplification step is optional, it is desirable in the preferred method of the invention.

The term "modifies" as used herein means the conversion of an unmethylated cytosine to another nucleotide which will distinguish the unmethylated from the methylated cytosine. Preferably, the agent modifies unmethylated cytosine to uracil. Preferably, the agent used for modifying unmethylated cytosine is sodium bisulfite, however, other agents that similarly modify unmethylated cytosine, but not methylated cytosine can also be used in the method of the invention. Sodium bisulfite ($NaHSO_3$) reacts readily with the 5,6-double bond of cytosine, but poorly with methylated cytosine. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by Taq polymerase and therefore upon PCR, the resultant product contains cytosine only at the position where 5-methylcytosine occurs in the starting template DNA.

The primers used in the invention for amplification of the CpG-containing nucleic acid in the specimen, after bisulfite modification, specifically distinguish between untreated DNA, methylated, and non-methylated DNA. MSP primers for the non-methylated DNA preferably have a T in the 3' CG pair to distinguish it from the C retained in methylated DNA, and the compliment is designed for the antisense primer. MSP primers usually contain relatively few Cs or Gs in the sequence since the Cs will be absent in the sense primer and the Gs absent in the antisense primer (C becomes modified to U (uracil) which is amplified as T (thymidine) in the amplification product).

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxy ribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the invention are designed to be "substantially" complementary to each strand of the genomic locus to be amplified and include the appropriate G or C nucleotides as discussed above. This means that the primers must be sufficiently complementary to hybridize with their respective strands under conditions which allow the agent for polymerization to perform. In other words, the primers should have sufficient complementarity with the 5' and 3' flanking sequences to hybridize therewith and permit amplification of the genomic locus.

Oligonucleotide primers of the invention are employed in the amplification process which is an enzymatic chain reaction that produces exponential quantities of target locus relative to the number of reaction steps involved. Typically, one primer is complementary to the negative (−) strand of the locus and the other is complementary to the positive (+) strand. Annealing the primers to denatured nucleic acid followed by extension with an enzyme, such as the large fragment of DNA Polymerase I and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing the target locus (e.g., CpG). Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The nucleic acid-containing specimen used for detection of methylated CpG may be from any source including brain, colon, urogenital, hematopoietic, thymus, testis, ovarian, uterine, prostate, breast, colon, lung and renal tissue and may be extracted by a variety of techniques such as that described by Maniatis, et al. (Molecular Cloning: A Laboratory Manual, Cold Spring Harbor, N.Y., pp 280, 281, 1982).

If the extracted sample is impure (such as plasma, serum, or blood or a sample embedded in parrafin), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80.degree. to 105.degree. C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405-437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7-9, most preferably about 8. Preferably, a molar excess (for genomic nucleic acid, usually about 10.sup.8:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90.degree.-100.degree. C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40.degree. C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

Preferably, the method of amplifying is by PCR, as described herein and as is commonly used by those of ordinary skill in the art. Alternative methods of amplification have been described and can also be employed as long as the methylated and non-methylated loci amplified by PCR using the primers of the invention is similarly amplified by the alternative means.

The amplified products are preferably identified as methylated or non-methylated by sequencing. Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008-1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229-237, 1988

Optionally, the methylation pattern of the nucleic acid can be confirmed by restriction enzyme digestion and Southern blot analysis. Examples of methylation sensitive restriction endonucleases which can be used to detect 5'CpG methylation include SmaI, SacII, EagI, MspI, HpaII, BstUI and BssHII, for example.

Treatment of Methylated SPARC Gene Related Cancers

DNMT inhibitors, such as 5-aza-cytidine (5-aza-CR) and 5-aza-2'-deoxycytidine (5-aza-CdR) are also widely studied because DNA hypomethylation induces the re-activation of tumor suppressor genes that are silenced by methylation-mediated mechanisms, and in particular, the methylated SPARC gene. The combination of HDAC inhibitors or demethylating agents with other chemo-therapeutics can be used as a possible molecularly targeted therapeutic strategy. In particular, the combination of HDAC inhibitors with demethylating agents are effective since histones are connected to DNA by both physical and functional interactions. As such, the combination of HDAC and DNMT inhibition can be very effective (and synergistic) in inducing apoptosis, differentiation and/or cell growth arrest in human pancreatic lung, breast, thoracic, leukemia and colon cancer cell lines. Effective agents include HDAC inhibitors, such as trichostatin A (TSA), sodium butyrate, depsipeptide (FR901228, FK228), valproic acid (VPA) and suberoylanilide hydroxamic acid (SAHA), and the demethylating agent, 5-aza-CdR used alone and in combination treatment of human cancer cells.

Diagnostic Kits

In another aspect, the invention provides kits for diagnosis of human cancer, wherein the kits can be used to detect the biomarker of the present invention. For example, the kits can be used to detect the methylated SPARC nucleic acid described herein, which biomarker is present in samples of a human cancer patient and not in normal subjects. The kits of the invention have many applications. For example, the kits can be used to differentiate if a subject has human cancer or has a negative diagnosis, thus aiding a human cancer diagnosis. In another example, the kits can be used to identify compounds that modulate expression of the biomarker in in vitro or in vivo animal models for human cancer.

Optionally, the kit may further comprise a standard or control information so that the test sample can be compared with the control information standard to determine if the test-amount of a biomarker detected in a sample is a diagnostic amount consistent with a diagnosis of human cancer.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

EXAMPLES

Materials and Methods

Materials

Amonoclonal anti-SPARC antibody (clone ON1-1) was purchased from Zymed Laboratories, Inc. (South San Francisco, Calif.). 5-Aza-2'-deoxycytidine (5Aza-dC) and human recombinant transforming growth factor (TGF)-β1 were purchased from Sigma Chemical Co. (St. Louis, Mo.). Purified human platelet SPARC protein was purchased from Calbiochem (Cambridge, Mass.).

Cell Lines and Tissue Samples

Seventeen human pancreatic cancer cell lines (AsPC1, BxPC3, Capan1, Capan2, CFPAC1, Colo357, Hs766T, MiaPaCa2, Panc1, PL1, PL3, PL6, PL9, PL10, PL11, PL12, and PL13) were maintained in RPMI 1640 (Invitrogen, Carlsbad, Calif.) supplemented with 10% fetal bovine serum (FBS), streptomycin, and penicillin at 37° C. in a humidified atmosphere containing 5% $CO_2$. An immortal cell line derived from normal human pancreatic ductal epithelium (HPDE) was generously provided by Dr. Ming-Sound Tsao (University of Toronto, Ontario) and maintained in Keratinocyte-SFM (Invitrogen). Primary fibroblasts were initially outgrown from chronic pancreatitis tissue from a 33-year-old male patient (panc-f1), from non-cancerous pancreatic tissue from a 61-year-old female patient with pancreatic cancer (panc-f3), or from pancreatic adenocarcinoma tissue from a 55-year-old female patient (panc-f5). These fibroblast cultures were carefully evaluated by light microscopy to exclude epithelial cell contamination, maintained in RPMI 1640 with 10% FBS, and used at 5-10 passages. Formalin-fixed paraffin-embedded blocks of 25 primary pancreatic adenocarcinomas resected at The Johns Hopkins Hospital were selected on the basis of tissue availability. Pancreatic cancer xenografts were established from surgically resected primary pancreatic carcinomas (Hahn et al., 1995), and 24 xenografts were randomly selected for this study. Normal pancreatic duct epithelial cells were selectively microdissected from resected pancreata from 10 patients (mean age, 64.3 years; range, 36-83) with various pancreatic disorders using a laser-capture microdissection (LCM) system. Serum samples from patients with pancreatic disease.

Oligonucleotide Array Hybridization and Data Analysis

Total RNA was isolated from cultured cells or frozen tissues using TRIZOL reagent (Invitrogen, Carlsbad, Calif.). First- and second-stranded cDNA was synthesized from 10 μg of total RNA using T7-$(dT)_{24}$ primer (SEQ ID NO: 14) (Genset Corp., South La Jolla, Calif.) and SuperScript Choice system (Invitrogen). Labeled cRNA was synthesized from the purified cDNA by in vitro transcription (IVT) reaction using the BioArray HighYield RNA Transcript Labeling Kit (Enzo Diagnostics, Inc., Farmingdale, N.Y.) at 37° C. for 6 hours, and was purified using RNeasy Mini Kit (QIAGEN, Valencia, Calif.). The cRNA was fragmented at 94° C. for 35 minutes in a fragmentation buffer (40 mmol/L Tris-acetate (pH 8.1), 100 mmol/L potassium acetate, 30 mmol/L magnesium acetate). The fragmented cRNA was then hybridized to the Human Genome U133A chips (Affymetrix, Santa Clara, Calif.) with 18,462 unique gene/EST transcripts at 45° C. for 16 hours. The washing and staining procedure was performed in the Affymetrix Fluidics Station according to the manufacturer's instructions. The probes were then scanned using a laser scanner, and signal intensity for each transcript (background-subtracted and adjusted for noise) and detection call (present, absent, or marginal) were determined using Microarray Suite Software 5.0 (Affymetrix).

Reverse-Transcription Polymerase Chain Reaction (RT-PCR)

Four µg of total RNA was reverse-transcribed using Superscript II (Invitrogen). The SPARC RT-PCR reaction was performed under the condition as follow: 95° C. for 5 minutes; then 28 cycles of 95° C. for 20 seconds, 63° C. for 20 seconds, and 72° C. for 20 seconds; and a final extension of 4 minutes at 72° C. Primer sequences were 5'-AAG ATC CAT GAG AAT GAG AAG-3' (forward) (SEQ ID NO: 11) and 5'-AAA AGC GGG TGG TGC AAT G-3' (reverse) (SEQ ID NO: 12). To check the integrity of mRNA, glyceraldehyde-3-phosphate dehydrogenase (GAPDH) was also amplified in the same PCR condition. For semiquantitative analysis, the RT-PCR was performed with primers for SPARC and GAPDH in duplex reactions, and range of linear amplification for both genes was examined with serial PCR cycles to determine the optimal cycle. The relative intensity of SPARC mRNA expression was then corrected for variable RNA recovery using the corresponding GAPDH mRNA measurement as a surrogate for total mRNA.

Immunohistochemistry

Five-µm sections were cut onto coated slides and deparaffinized by routine techniques. Antigen retrieval was performed in 10 mM sodium citrate buffer (pH 6.0) heated at 95° C. in a steamer for 20 minutes. After blocking endogenous peroxidase activity with a 3% aqueous $H_2O_2$ solution for 5 minutes, the sections were incubated with an anti-SPARC monoclonal antibody at a final concentration of 4 µg/ml for 60 minutes. Labeling was detected with the Envision Plus Detection Kit (DAKO, Carpinteria, Calif.) following the protocol as suggested by the manufacturer, and all sections were counterstained with hematoxylin. The extent of immunolabeling of SPARC was categorized into three groups: 0%, negative; = or <10%, focal; and >10%, positive. The intensity of immunolabeling was categorized as weak (+), moderate (+$^+$), or strong (++$^+$).

Methylation-Specific Polymerase Chain Reaction (MSP)

Methylation status of the SPARC gene was determined by MSP as described previously (Herman et al., 1996). Briefly, 1 µg of genomic DNA was treated with sodium bisulfite for 16 hours at 50° C. After purification, 1 µl of the bisulfite-treated DNA was amplified using primers specific for either the methylated or for the unmethylated DNA under the conditions as follows: 95° C. for 5 minutes; then 40 cycles of 95° C. for 20 seconds, 62° C. for 20 seconds, and 72° C. for 30 seconds; and a final extension of 4 minutes at 72° C. Primer sequences were TTT TTT AGA TTG TTT GGA GAG TG (forward) (SEQ ID NO: 4) and AAC TAA CAA CAT AAA CAA AAA TAT C (reverse) (SEQ ID NO: 5) for unmethylated reactions (132 bp), and GAG AGC GCG TTT TGT TTG TC (forward) (SEQ ID NO: 6) and AAC GAC GTA AAC GAA AAT ATC G (reverse) (SEQ ID NO: 7) for methylated reactions (112 bp). Five µl of each PCR product were loaded onto 3% agarose gels and visualized by ethidium bromide staining.

5Aza-dC Treatment

Eight pancreatic cancer cell lines (AsPC1, BxPC3, Capan2, CFPAC1, Hs766T, MiaPaCa2, PL3, and PL12) were treated with 5Aza-dC. Cells in log phase growth were seeded in T-75 culture flasks. After overnight incubation, the cells were exposed continuously to 5Aza-dC (1 µM) for 4 days, with a change of drug and culture medium every 24 hours.

SPARC Enzyme-Linked Immunosorbent Assay (ELISA)

Cells were seeded at a density of $1 \times 10^5$ cells/well in 6-well plates. After overnight incubation, the cells were washed with phosphate-buffered saline (PBS) and incubated in 2 ml of serum-free medium for 24 hours. The conditioned media were harvested and centrifuged to remove cellular debris. SPARC concentration in the conditioned media was measured using an enzyme-linked immunosorbent assay (ELISA) kit (Haematological Technologies, Inc., Essex Junction, Vt.) according to the manufacturer's instructions. SPARC levels were measured in the serum of patients with pancreatic disease in similar fashion.

Treatment of Pancreatic Cancer Cells with SPARC

We treated two pancreatic cancer cell lines (AsPC1 and Panc1) with exogenous SPARC. Cells in log phase growth were seeded at a density of $1 \times 10^4$ cells/well in 24-well plates. After overnight incubation, cells were treated with or without human platelet SPARC protein (10 µg/ml) for 72 hours, and the number of cells were counted by hemacytometer in three independent wells.

Fibroblasts/Pancreatic Cancer Cells Co-Culture

Fibroblasts were seeded in 6-well plates and grown for 48-72 hours. Pancreatic cancer cells (CFPAC1) were then seeded into the upper chamber of a transwell apparatus (Becton Dickinson, Franklin Lakes, N.J.), which physically separated the tumor cells from the fibroblasts but allowed for interaction between the cells via soluble factors. After 48-hour incubation, fibroblasts were washed with PBS and harvested by trypsinization.

Statistical Analysis

Statistical analysis was performed using Fisher's exact probability test or unpaired Student's t test (two-tailed). Differences were considered significant at $P<0.05$.

Example 1

Gene Expression Analysis of SPARC in Pancreatic Cancer by Serial Analysis of Gene Expression (SAGE) and Oligonucleotide Microarrays Oligonucleotide microarrays have been used to identify genes that are induced 5-fold or greater by treatment of pancreatic cancer cells with 5Aza-dC (Sato et al., manuscript submitted). SPARC was one of the genes we identified using this approach. We therefore analyzed the gene expression and methylation status of the SPARC gene in pancreatic cancer. First, we searched an online SAGE database (http://www.ncbi.nlm.nih.gov/SAGE/) to determine the gene expression patterns of SPARC in short-term cultures of normal pancreatic ductal epithelium, pancreatic cancer cell lines, and primary pancreatic cancer tissues. The SAGE Tag to Gene Mapping analysis showed that the Hs.111779 tag (ATGT-GAAGAG (SEQ ID NO: 13)) corresponding to the SPARC gene was present in both of two libraries from normal pancreatic duct epithelial cell cultures (H126 and HX), whereas the SPARC tag was not identified in 3 of 4 pancreatic cancer cell lines (FIG. 1A). By contrast, the SPARC tag was detected at high levels in two primary pancreatic adenocarcinoma tissues (Panc 91-16113 and Panc 96-6252), suggesting that this gene may be an "invasion-specific gene" a gene whose expression is specifically identified in tissue specimens of invasive pancreatic cancer but not in passaged pancreatic cancer cell lines (Ryu et al., 2001).

We then determined the SPARC expression by analyzing global gene expression profiling (U133A oligonucleotide microarrays, Affymetrix) in two frozen tissue samples of normal pancreatic ductal epithelial cells selectively microdissected by LCM, a non-neoplastic pancreatic epithelial cell line (HPDE), and 5 pancreatic cancer cell lines (AsPC1, CFPAC1, Hs766T, MiaPaCa2, and Panc1). The SPARC transcript was detected in the normal pancreatic ductal epithelial cells and HPDE (FIG. 1B). In contrast, SPARC was not expressed in 4 of the 5 pancreatic cancer cell lines.

Example 2

Expression of SPARC mRNA in Pancreatic Cancer Cell Lines and Primary Fibroblasts RT-PCR was preformed to examine the expression of SPARC mRNA in a panel of 17 pancreatic cancer cell lines and in primary fibroblasts derived from pancreatic adenocarcinoma tissue (panc-f5). The SPARC transcript was detectable in a non-neoplastic pancreatic ductal epithelial cell line (HPDE) and was strongly expressed in the pancreatic cancer-derived fibroblasts, whereas the expression was absent in 15 (88%) of the 17 pancreatic cancer cell lines (FIG. 1C). Of note, the RT-PCR results of 7 pancreatic cancer cell lines (AsPC1, Capan1, Capan2, CFPAC1, Hs766T, MiaPaCa2, and Panc1) parallel the SAGE and/or oligonucleotide array data on these same cell lines. These results demonstrate the striking difference in SPARC expression between most pancreatic cancer cell lines and stromal fibroblasts.

Example 3

Immunohistochemical Analysis of SPARC Expression in Pancreatic Carcinoma

Figure 2:
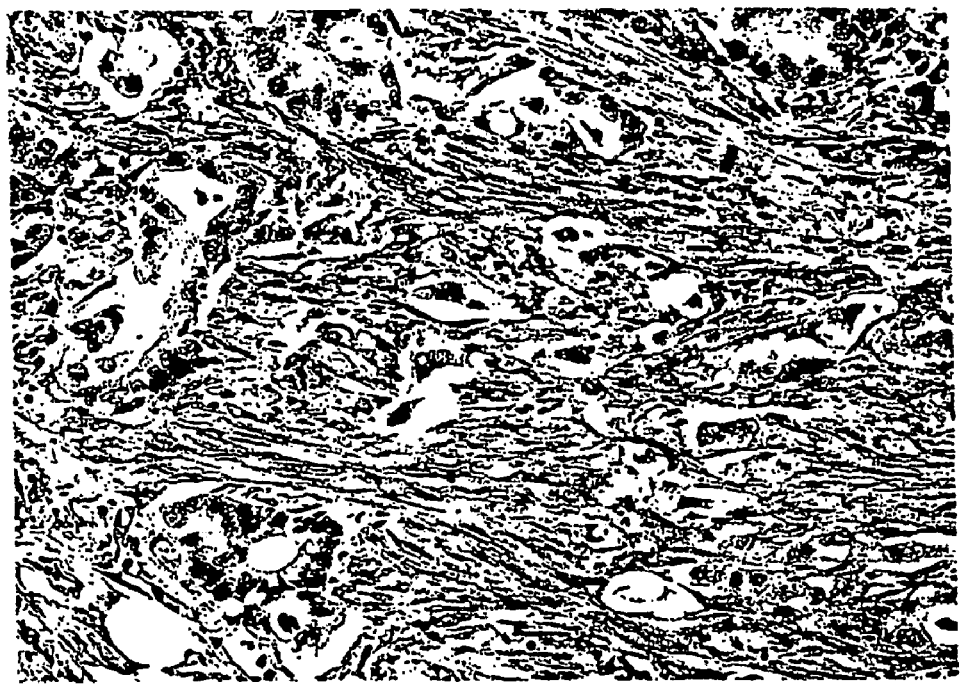
FIG. 2 represents immunohistochemical staining for SPARC in pancreatic adenocarcinoma (A, ×50; B and C, ×160). Strong cytoplasmic labeling is detected in the stromal cells, in contrast to the neoplastic epithelium that is negative for SPARC.

The expression of SPARC protein was examined in 25 primary pancreatic adenocarcinoma tissues by immunohistochemical labeling with an anti-SPARC monoclonal antibody. In 19 (76%) of 25 cases, moderate (++) to strong (+++) SPARC expression was found in the peritumoral stromal cells, presumably fibroblasts, and positive immunolabeling was identified as dark brown granules throughout the cytoplasm (FIG. 2). In these cases, the expression was most pronounced in the stromal fibroblasts immediately adjacent to the neoplastic epithelium, whereas the staining was weak or absent in the stroma distant from the infiltrating carcinoma. Immunolabeling of SPARC was also observed in neoplastic epithelium in 8 (32%) of 25 cases, but the labeling was weak and focal, with the exception of a single case in which 50% of the neoplastic cells strongly labeled. In the remaining 17 cases (68%), neoplastic cells did not label for SPARC throughout the tumor (FIG. 2). The immunoreactivity in normal ductal epithelium was variable among cases; some normal ductal cells showed weak cytoplasmic staining but others did not. These immunohistochemical findings suggest that the increased SPARC tags detected in the SAGE libraries of the primary pancreatic cancer tissues originated primarily from stromal fibroblasts.

Example 4

Methylation Analysis of SPARC Gene in Pancreatic Cancer

Figure 3:
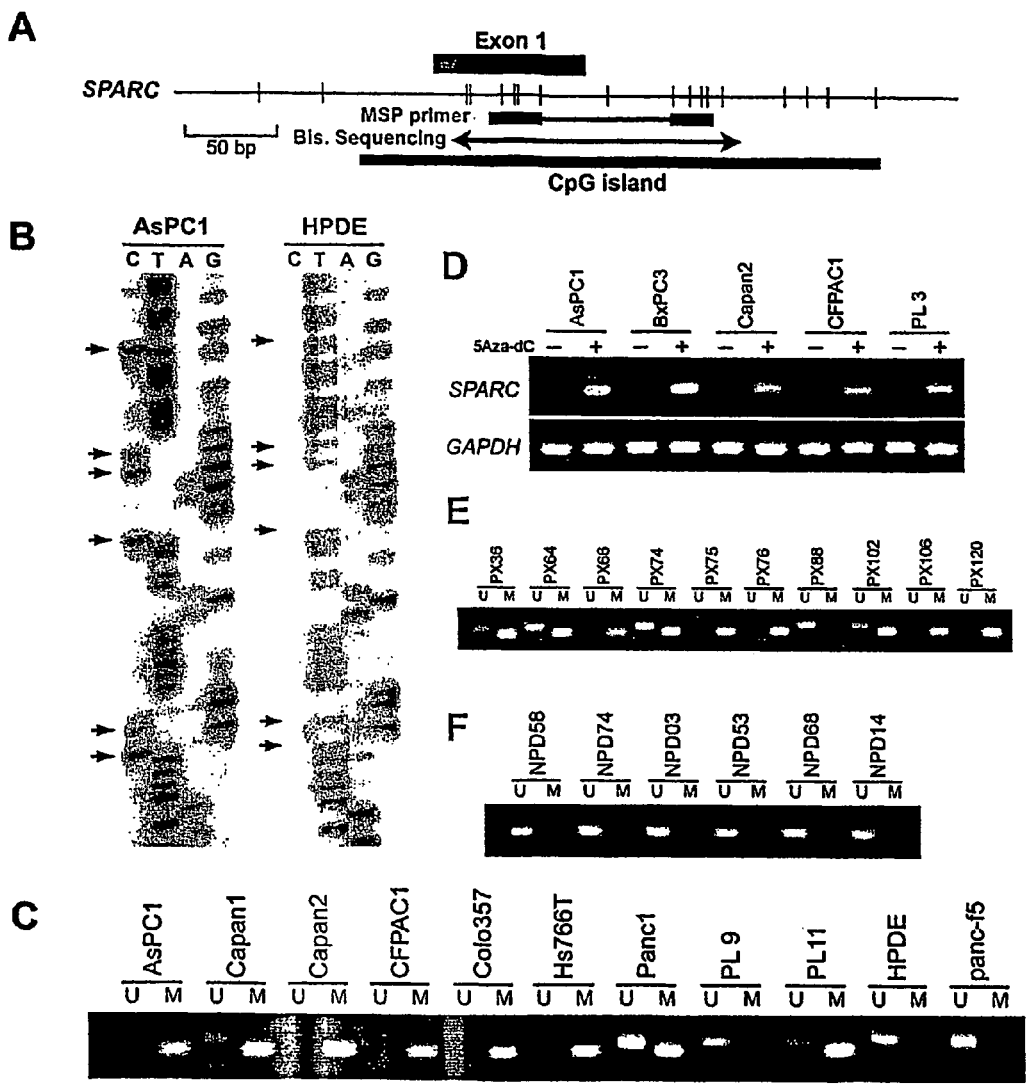
FIG. 3 represents (a) Distribution of CpG dinucleotides (vertical lines) in the 5' region of the SPARC gene showing a CpG-rich sequence (CpG island) spanning from exon 1 to intron 1; (b) Methylation-specific PCR (MSP) analysis of SPARC in pancreatic cancer cell lines and a non-neoplastic HPDE; the PCR products in the lanes U and M indicate the presence of umethylated and methylated templates, respectively; (c) SPARC mRNA expression by RT-PCR in pancreatic cancer cell lines harboring aberrant SPARC methylation before (−) and after (+) treatment with 5-aza-2'-deoxycytidie (SAza-dC); (d) MSP analysis of SPARC in pancreatic cancer xenografts; (e) MSP analysis of SPARC in normal pancreatic ductal epithelia selectively microdissected. (f) MSP analysis of SPARC in the identified cell lines.

We next analyzed the methylation status of the SPARC gene in a panel of 17 pancreatic cancer cell lines. SPARC has a relatively CpG-rich sequence spanning from exon 1 to intron 1 (GC content of 64%, ratio of CpG to GpC of 0.6, and a length of 279 bp), which fulfills the criteria of CpG island (FIG. 3A). Using MSP, we found that the SPARC CpG island was aberrantly methylated in 16 (94%) of the 17 pancreatic cancer cell lines (FIG. 3B). The methylation status of SPARC correlated with its expression, and 15 (94%) of the 16 cell lines with aberrant methylation demonstrated absent mRNA expression. By contrast, methylated alleles were not identified in fibroblasts, in a non-neoplastic ductal cell line (HPDE), or in a pancreatic cancer cell line (PL9) with high mRNA expression (P=0.004).

To confirm that DNA methylation is a mechanism for the silencing of SPARC, we treated 8 pancreatic cancer cell lines harboring SPARC methylation with the demethylating agent 5Aza-dC. The SPARC mRNA expression was restored in 7 of the 8 cell lines after 5Aza-dC treatment (FIG. 3C). In one cell line (Hs766T); however, 5Aza-dC treatment did not restore the SPARC expression. Furthermore, treatment of Hs766T with the histone deacetylase inhibitor trichostatin A (TSA) or with a combination of 5Aza-dC and TSA did not induce the SPARC expression (data not shown). These results suggest that other mechanisms besides DNA methylation and histone deacetylation may be involved in the silencing of SPARC in this cell line.

The methylation status of SPARC was also analyzed in a panel of 24 xenograft tumors established from human primary pancreatic carcinomas and compared it to methylation patterns in 10 normal pancreatic ductal epithelia selectively microdissected by LCM. Aberrant methylation of SPARC was detected in 21 (88%) of the 24 pancreatic xenografts (FIG. 3D), whereas none of the 10 normal ductal epithelium samples displayed methylated alleles (FIG. 3E). These results confirm the abnormal methylation pattern of SPARC in primary pancreatic carcinomas as well as in pancreatic cancer cell lines.

Example 5

Effect of SPARC on Proliferation of Pancreatic Cancer Cells

Since SPARC is a secreted protein and has multiple biological functions, the altered patterns of SPARC expression in pancreatic cancer cells and stromal fibroblasts could affect tumor progression at the site of tumor-host interface. Based on the expression data, we hypothesized that SPARC protein is secreted from stromal fibroblasts within invasive pancreatic carcinoma. To test this hypothesis, we measured the SPARC concentration in conditioned media from three pancreatic cancer cell lines (AsPC1, BxPC3, and Panc1) and fibroblasts derived from pancreatic cancer (panc-f5) by ELISA. The amount of SPARC secretion was negligible (0-30 ng/ml) in media from AsPC1 and BxPC3 with no detectable mRNA expression, and a slightly higher secretion of SPARC protein (~100 ng/ml) was found in Panc1 with detectable mRNA expression. The highest SPARC secretion (~1400 ng/ml) was identified in the fibroblast cultures. These results demonstrate a correlation between SPARC mRNA expression and the amount of SPARC secretion in vitro.

Figure 4:
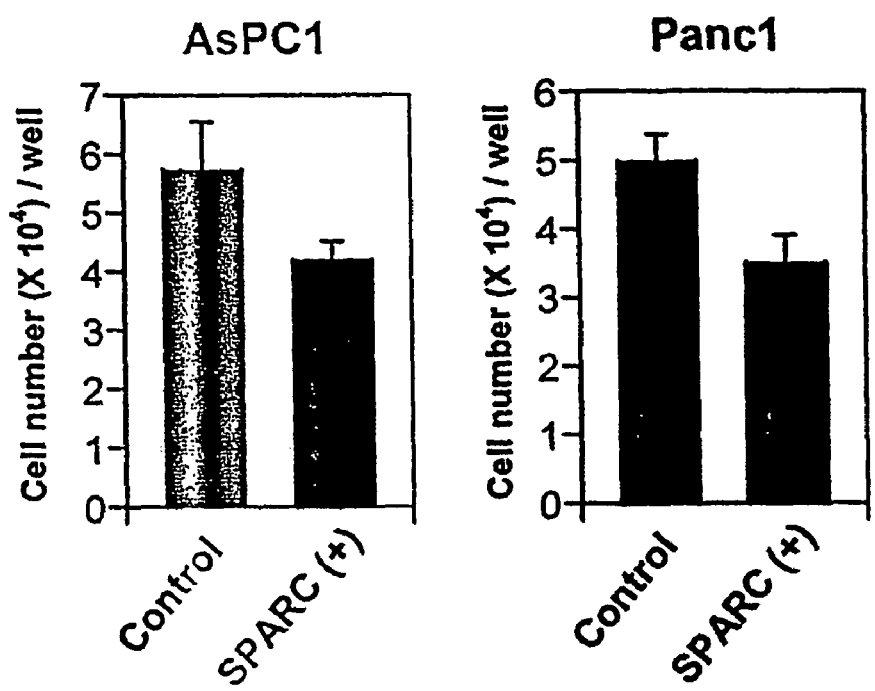
FIG. 4 represents the effects of exogenous SPARC on proliferation of pancreatic cancer cells in vitro; two pancreatic cancer cell lines (AsCP1 and Panc1) were treated with or without SPARC (10 μg/ml), and cell number was counted 72 hours after treatment; the cell numbers shown are the means±SD of six measurements from three independent wells.

The effect of exogenous SPARC protein on growth of pancreatic cancer cells in vitro was also examined. We treated two pancreatic cancer cell lines (AsPC1 and Panc1) with purified SPARC protein and counted the number of cells after 72 hours. Treatment with exogenous SPARC (10 μg/ml) significantly suppressed the growth of AsPC1 cells by ~27% (5.8±0.8 versus 4.2±0.3 ($\times 10^4$ cells), P=0.001) (FIG. 4). Similarly, exposure of Panc1 cells to SPARC (10 μg/ml) resulted in growth inhibition by ~30% (5.0±0.4 versus 3.5±0.4 ($\times 10^4$ cells), P<0.0001) (FIG. 4). Thus, these results suggest that exogenous SPARC protein has growth-suppressive activity on pancreatic cancer cells.

Example 6

Serum SPARC Levels in Patients with Pancreatic Disease

The concentration of SPARC protein was measured in serum samples from 20 patients with pancreatic adenocarcinoma, 20 patients with benign pancreatic disorders, and 20 healthy individuals by ELISA. There was no significant difference in the mean SPARC levels among these three groups (data not shown).

Example 7

Effects of Tumor-Stromal Interactions on SPARC Expression in Fibroblasts

Figure 5:
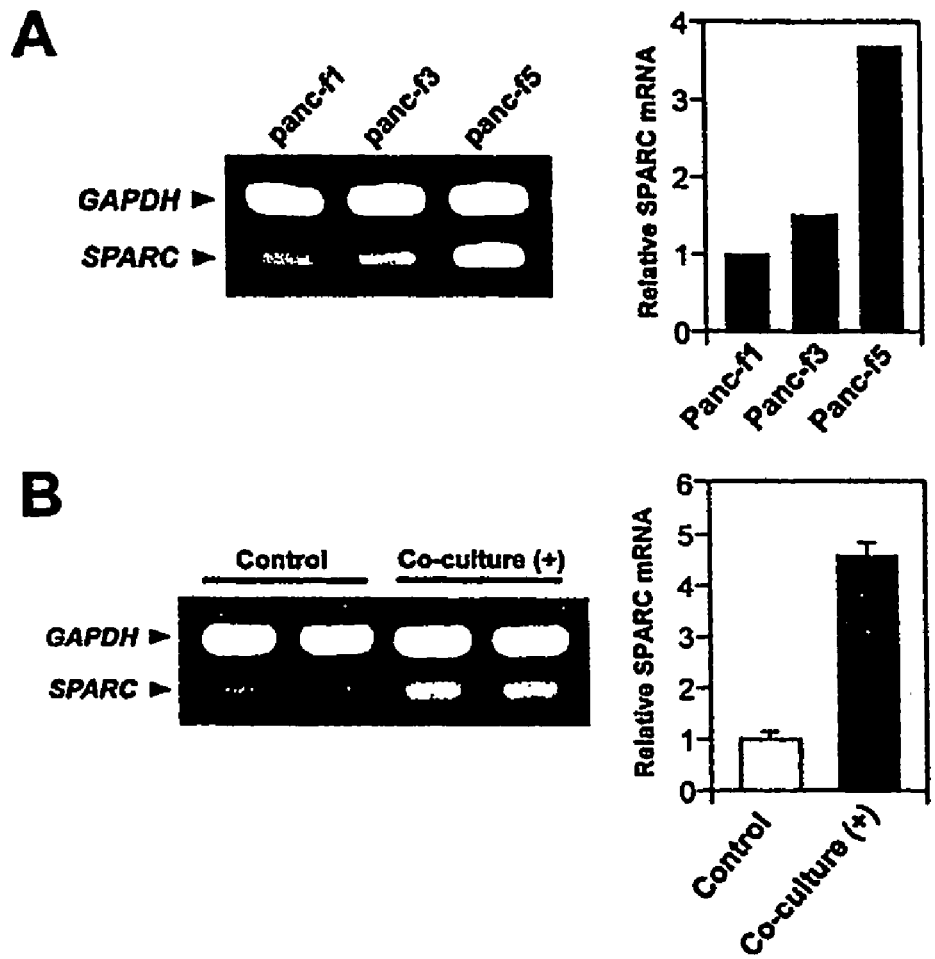
FIG. 5 represents (a) Semiquantitative RT-PCR analysis of SPARC expression in primary fibroblasts derived from chronic pancreatitis tissue (panc-f1), from non-cancerous pancreatic tissue from a patient with pancreatic cancer (panc-f3), and from pancreatic adenocarcinoma tissue (panc-f5); the bar graph shown represents relative SPARC mRNA expression for each sample normalized to the corresponding GAPDH expression; (b) Change in SPARC mRNA expression in fibroblasts (panc-f3) upon co-culture with pancreatic cancer cells (CFPAC1); the bar graph represents the mean.+−.SD of relative SPARC expression levels (normalized to GAPDH) from two independent PCR reactions.

To elucidate the relationship between tumor-host interactions and transcriptional regulation of SPARC in stromal fibroblasts, the SPARC mRNA expression was compared in three primary fibroblast cultures derived from different histological types of pancreatic tissues. Using semi-quantitative RT-PCR, we found that fibroblasts derived from chronic pancreatitis tissue (panc-f1) and those from non-cancerous pancreatic tissue from a patient with pancreatic cancer (panc-f3) showed weaker expression of SPARC mRNA compared to fibroblasts derived from pancreatic cancer tissue (panc-f5) (FIG. 5A). These results, together with the immunohistochemical finding of SPARC expression localized to the peritumoral stroma, have led us to hypothesize that SPARC expression in the stromal fibroblasts is modulated by interactions with tumor cells. To directly test this hypothesis, we utilized a co-culture system in which fibroblasts (panc-f3) and pancreatic cancer cells (CFPAC1) can communicate via soluble factors. SPARC mRNA expression in panc-f3 was markedly (~4,6-fold) augmented when these cells were co-cultured with pancreatic cancer cells (FIG. 5B). Thus, the SPARC transcription in the fibroblasts can be up-regulated in response to soluble mediators secreted by pancreatic cancer cells.

Because several growth factors such as TGF-β are known to induce the SPARC expression in fibroblasts (Wrana et al., 1991; Reed et al., 1994), and because TGF-β is one of the major secreted proteins highly expressed by pancreatic cancer cells (Friess et al., 1993), we examined the effect of TGF-β on SPARC expression in fibroblasts (panc-f3). When the fibroblasts were incubated with TGF-β (5 ng/ml) for 24 hours, the SPARC mRNA expression was increased by ~3,3-fold (FIG. 5C), indicating that TGF-β may be a candidate of tumor-derived factors that stimulate the transcription of SPARC in stromal fibroblasts in a paracrine fashion. We also treated two pancreatic cancer cell lines with differing endogenous SPARC expression (AsPC1 with no mRNA expression and Panc1 with detectable expression) with TGF-β (5 ng/ml). After treatment, a slight increase (~1,5-fold increase) in the SPARC mRNA expression was observed in Panc1, whereas the transcript remained undetectable in AsPC1 (data not shown).

REFERENCES

Bellahcene A and Castronovo V. (1995). *Am. J. Pathol.*, 146, 95-100.
Bradshaw A D, Francki A, Motamed K, Howe C and Sage E H. (1999). *Mol. Biol. Cell*, 10, 1569-1579.
Bradshaw A D and Sage E H. (2001). *J. Clin. Invest.*, 107, 1049-1054.
Brekken R A, Puolakkainen P, Graves D C, Workman G, Lubkin S R and Sage E H. (2003). *J. Clin. Invest.*, 111, 487-495. 482: Francki A, et al. SPARC regulates cell cycle pr . . . [PMD:12577314] Related Articles, Links.
Brekken R A and Sage E H. (2001). *Matrix Biol.*, 19, 816-827.
Briggs J, Chamboredon S, Castellazzi M, Kerry J A and Bos T J. (2002). *Oncogene*, 21, 7077-7091.
Chambers R C, Leoni P, Kaminsid N, Laurent G J and Heller R A. (2003). Am. J. Pathol., 162, 533-546.
Dhanesuan N, Sharp J A, Blick T, Price J T and Thompson E W. (2002). Breast Cancer Res. Treat., 75, 73-85.
Francki A, Bradshaw A D, Bassuk J A, Howe C C, Couser W G and Sage E H. (1999). *J. Biol. Chem.*, 274, 32145-32152.
Francki A, Motamed K, McClure T D, Kaya M, Murri C, Blake-D J, Carbon J G and Sage E H. (2003). *J. Cell. Biochem.*, 88, 802-811.
Friess H, Yamanaka Y, Buchler M, Ebert M, Beger H G, Gold L I and Korc M. (1993). *Gastroenterology*, 105, 1846-1856.
Fukushima N, Sato N, Ueki T, Rosty C, Walter K M, Wilentz R E, Yeo C J, Hruban R H and Goggins M. (2002). *Am J Pathol*, 160, 1573-1581.
Funk S E and Sage E H. (1991). *Proc. Natl. Acad. Sci. USA*, 88, 2648-2652.
Funk S E and Sage E H. (1993). *J. Cell Physiol.*, 154, 53-63.
Hahn S A, Seymour A B, Hoque A T, Schutte M, da Costa L T, Redston M S, Caldas C, Weinstein C L, Fischer A, Yeo C J, Hruban R H and Kern S E. (1995). *Cancer Res.*, 55, 4670-4675.
Herman J G, Graff J R, Myohanen S, Nelkin B D and Baylin S B. (1996). *Proc. Natl. Acad. Sci. USA*, 93, 9821-9826.
Iacobuzio-Donahue C A, Argani P, Hempen P M, Jones J and Kern S E. (2002a). *Cancer Res.*, 62, 5351-5357.
Iacobuzio-Donahue C A, Ryu B, Hruban R H and Kern S E. (2002b). *Am. J. Pathol.*, 160, 91-99.
Jacob K, Webber M, Benayahu D and Kleinman H K. (1999). *Cancer Res.*, 59, 4453-4457.
Jansen M, Fukushima N, Rosty C, Walter K, Altink R, Heek T V, Hruban R, Offerhaus J G and Goggins M. (2002). *Cancer Biol Ther*, 1, 293-296.
Jendraschak E and Sage E H. (1996). *Semin Cancer Biol*, 7, 139-146.
Jones P A and Baylin S B. (2002). *Nat. Rev. Genet.*, 3, 415-428.
Le Bail B, Faouzi S, Boussarie L, Guirouilh J, Blanc J F, Carles J, Bioulac-Sage P, Balabaud C and Rosenbaum J. (1999). *J. Pathol.*, 189, 46-52.

Ledda F, Bravo A I, Adris S, Bover L, Mordoh J and Podhajcer O L. (1997). *J. Invest. Dennatol.,* 108, 210-214.

Maehara N, Matsumoto K, Kuba K, Mizumoto K, Tanaka M and Nakamura T. (2001). *Br. J. Cancer.,* 84, 864-873.

Massi D, Franchi A, Borgognoni L, Reali U M and Santucci M. (1999). *Hum. Pathol.,* 30, 339-344.

Mok S C, Chan W Y, Wong K K, Muto M G and Berkowitz R S. (1996). *Oncogene,* 12, 1895-1901.

Paley P J, Goff B A, Gown A M, Greer B E and Sage E H. (2000). *Gynecol. Oncol.,* 78, 336-341.

Porte H, Chastre E, Prevot S, Nordlinger B, Empereur S, Basset P, Chambon P and Gespach C. (1995). *Int. J. Cancer,* 64, 70-75.

Porte H, Triboulet J P, Kotelevets L, Carrat F, Prevot S, Nordlinger B, DiGioia Y, Wurtz A, Comoglio P, Gespach C and Chastre E. (1998). *Clin. Cancer Res.,* 4, 1375-1382.

Porter P L, Sage E H, Lane T F, Funk S E and Gown A M. (1995). *J. Histochem. Cytochem.,* 43, 791-800.

Reed M J, Vernon R B, Abrass I B and Sage E H. (1994). *J Cell Physiol.,* 158, 169-179.

Rempel S A, Ge S and Gutierrez J A. (1999). *Clin. Cancer Res.,* 5, 237-241.

Rosty C, Christa L, Kuzdzal S, Baldwin W M, Zahurak M L, Carnot F, Chan D W, Canto M, Lillemoe K D, Cameron J L, Yeo C J, Hruban R H and Goggins M. (2002). *Cancer Res.,* 62, 1868-1875.

Ryu B, Jones J, Hollingsworth M A, Hruban R H and Kern S E. (2001). Cancer Res., 61, 1833-1838.

Sato N, Ueki T, Fukushima N, Iacobuzio-Donahue C A, Yeo C J, Cameron J L, Hruban R H and Goggins M. (2002). *Gastroenterology,* 123, 365-372.

Schultz C, Lemke N, Ge S, Golembieski W A and Rempel S A. (2002). *Cancer Res.,* 62, 6270-6277.

Thomas R, True L D, Bassuk J A, Lange P H and Vessella R L. (2000). *Clin. Cancer Res.,* 6, 1140-1149.

Ueki T. Toyota M, Skinner H, Walter K M, Yeo C J, Issa J P, Hruban R H and Goggins M. (2001). *Cancer Res.,* 61, 8540-8546.

Ueki T, Toyota M, Sohn T, Yeo C J, Issa J P, Hruban R H and Goggins M. (2000). *Cancer Res.,* 60, 1835-1839.

Ueki T, Walter K M, Skinner H, Jaffee E, Hruban R H and Goggins M. (2002). *Oncogene,* 21, 2114-2117.

Wewer U M, Albrechtsen R, Fisher L W, Young M F and Termine J D. (1988). *Am. J. Pathol.,* 132, 345-355.

Wrana J L, Overall C M and Sodek J. (1991). *Eur J. Biochem.,* 197, 519-528.

Yamanaka M, Kanda K, Li N C, Fukumori T, Oka N, Kanayama H O and Kagawa S. (2001). *J. Urol.,* 166, 2495-2499.

Yan Q and Sage E H. (1999). *J. Histochem. Cytochem.,* 47, 1495-1506.

Yiu G K, Chan W Y, Ng S W, Chan P S, Cheung K K, Berkowitz R S and Mok S C. (2001). *Am. J. Pathol.,* 159, 609-622.

What is claimed is:

1. A method for diagnosing pancreatic cancer, comprising the detection of a methylated SPARC nucleic acid molecule in a sample from a subject, wherein the methylated SPARC nucleic acid molecule has at least 90% sequence identity to the nucleic acid set forth in SEQ ID NO: 1 (FIG. 6), and wherein the sample is a pancreatic cell culture, a pancreatic tissue biopsy or a pancreatic juice sample.

2. The method of claim 1 wherein the presence of a methylated SPARC nucleic acid molecule is compared to a sample from a subject without cancer.

3. The method of claim 1 wherein the sample is obtained from a mammal suspected of having a pancreatic cancer.

4. The method of claim 1, wherein the methylated SPARC nucleic acid molecule has at least 95% sequence identity to the nucleic acid set forth in SEQ ID NO: 1 (FIG. 6).

5. The method of claim 1, wherein the nucleic acid molecule is expressed at a lower level in a patient with pancreatic cancer as compared to expression levels in a normal individual.

6. The method of claim 1, wherein the nucleic acid molecule is expressed at least 5 fold lower in a patient with pancreatic cancer as compared to expression in a normal individual.

7. The method of claim 1, wherein the nucleic acid molecule is expressed at least about 10 fold lower in a patient with pancreatic cancer as compared to expression in a normal individual.

8. The method of claim 1 wherein the subject sample is obtained from a mammalian patient.

9. The method of claim 1 wherein the subject sample is obtained from a human patient.

10. A method of claim 1 wherein the method of detecting a methylated SPARC nucleic acid comprising methylation specific polymerase chain reaction (MSP).

11. A method for detecting a methylated CpG-containing SPARC nucleic acid molecule, wherein the methylated SPARC nucleic acid molecule comprises the nucleic acid sequence set forth in SEQ ID NO: 1, the method comprising: contacting a nucleic acid-containing specimen with bisulfite to modify unmethylated cytosine to uracil; contacting the SPARC nucleic acid molecule with oligonucleotide primers that discriminate between methylated and unmethylated CpGs; and detecting the methylated CpGs in the nucleic acid, and wherein the specimen is from a pancreatic cell or tissue.

12. The method of claim 11, further comprising amplifying the CpG-containing nucleic acid in the specimen by means of the oligonucleotide primers.

13. The method of claim 12, wherein the amplifying step is the polymerase chain reaction (PCR).

14. The method of claim 11, wherein the CpG-containing nucleic acid is in a promoter region.

15. The method of claim 14, wherein the promoter is a tumor suppressor gene promoter.

16. A method for diagnosing pancreatic cancer, comprising the detection of a methylated SPARC nucleic acid molecule in a sample from a subject, wherein the nucleic acid molecule is expressed at least 5 fold lower in a patient with pancreatic cancer as compared to expression in a normal individual, and wherein the methylated SPARC nucleic acid molecule has at least 90% sequence identity to the nucleic acid set forth in SEQ ID NO: 1 (FIG. 6), and wherein the sample is a pancreatic cell culture, a pancreatic tissue biopsy or a pancreatic juice sample.

* * * * *

SEQUENCE LISTING

```
<160> NUMBER OF SEQ ID NOS: 14

<210> SEQ ID NO 1
<211> LENGTH: 2313
<212> TYPE: DNA
<213> ORGANISM: Homo sapiens

<400> SEQUENCE: 1
gaattccttg tactttttt cccttctcag ttctgcactt aactcgtcta aaaaaattaa      60
aaaagaattt aagaaaccac aaagctaagc tgggtgcggt ggctcacgcc tgtaatccta     120
gcactttggg aagccaaggc attcggattg cccaagctca ggagttcgag accagcctgg    180
gcaacatgtt gaaaccccat ttctactaaa aatacaataa attagctggg tgttgtggca    240
tgtgcgcctg taatcccagc tactctggag gctgaggcgc gataattgct tgaacccggg    300
aggcagaggt tgcagtgagc cgaaatcata ccactgcact ccagcctggg cgacagagtg    360
agtgagactc tgtctcaaaa caaaacaaaa caaacaaaca aaaaaccgg aaaccaacaa     420 aacttttga ggaacaaagg gaaccaggta ttttattaat tctcatacct ccagagtgtt     480
aggcacaaaa taaacattca accaagacct gttgcactga gcagttcata tataacagga    540
gtgacccaag ttgaaacgta gaatcagccc tctcatacca cttttttgcca ggtgatcata   600 ggcaagttac ttagcatcta tgtttcctta ttattaaaat ggtcataatt acaatgccta    660 agataaggg gttgctgtga agattattaa atcctcagta aactttggct attgttactc    720
ctatgattat catcaatatc atcaattacc ttatctgttc aatactggtg gcacaggtcc   780
accagctaga tgtctaatcc cttatgtgtc tattagtggt acaagtggag tttgagtggg    840
attttttttt ttttttttaa gaccagttcc aaatcatcaa ggatgatacc actagtagca    900
gcttgtcttg tctgtacagt ggtaagtcct ggccttgcct ttgtggcaaa tacaacccccc   960
```

-continued

```
ttgaattgct tggcccttct cagcattgcc taatattagg gaggactcct gtaaagctca    1020
ctggttagaa gatcaagaca cttgggcctg gttctgcccc tgggggccat tgggtaattc    1080
cttssagtct ccaggcctca cttgccctct gaacaagaaa gaggcctgtt ctggtcatcc    1140
ctccagcctg tccagccctg gcactctgtg agtcggttta ggcagcagcc ccggaacaga    1200
tgaggcaggc agggttggga cgtttggtca ggacagccca ccgcaaaaag aggaggaaag    1260
aaatgaaaga cagagacagc tttggctatg ggagaaggag gaggccgggg gaaggaggag    1320
acaggaggag gagggaccac ggggtggagg ggagatagac ccagcccaga gctctgagtg    1380
gtttcctgtt gcctgtctct aaacccctcc acattcccgc ggtccttcag actgcccgga    1440
gagcgcgctc tgcctgccgc ctgcctgcct gccactgagg tatgtgtgac ccccgcccag    1500 ccttttcсctt ctatagttgc accaaccccg acaccccgt tcacgccgtc agctcgtgtg    1560
caagggaggg aagctctgct gaggatgcgc ctctcctccc ggctccatca cggctcccct    1620
taagagcatg gccctcggtc ctgtctgcct gttgcttttc agaaggtgga ctcactgtgt    1680
aactttgtct tcccttacag gtttacagga aaataatctc actatgttct tcggggggagc    1740 attttctcac tctctgtttt tctctgtgtc tgtctctggt ttcagaggct gcctgcctgt    1800
cctctttgct ccctttgcaa atgtggcagc ctcctccttt cctgggaatc tgatcccatc    1860
acagctgcca cagggacctg gccagcaacc ggagtctgtc ctccagatct cggtcagggg    1920
ttctgttttc caaaaaggga ctttgcagaa caatcagttg atctctgaaa gggaaagggg    1980
gaggcttcac cattaatcca cacctctggg aagcttctgt tttcctctaa ttctcctcac    2040
tcccaaacac caccttccgt ccccccaata cacaaatttc agcaccattc tgcctgaaat    2100
ggcaccatca caacctcagt cttgggttag gtgttgttcc tgtcctgagt tccttgggat    2160
ggtaaacaca ggcagtagcc cttagtttat ctagatctga aaacccagac atcagatatc    2220
gtcaaccaag acatgggtgt aatgggaggt ggagtgtgct ggggggagata ttctcagaag    2280 ggggaaaggg ggaagggaag agggagagaa ttc                                2313
```

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atttagttta gagttttgag tgg                                            23

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 3
acaaaacttc cctcccttac                                                20

<210> SEQ ID NO 4
<211> LENGTH: 23
<212> TYPE: DNA
<213> ORGANISM: Artificial Sequence
<220> FEATURE:

```
<223> OTHER INFORMATION: Description of Artificial Sequence:
      Synthetic primer

<400> SEQUENCE: 4 tttttttagat tgtttggaga gtg                                              23

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 5
aactaacaac ataaacaaaa atatc                                             25

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 6
gagagcgcgt tttgtttgtc                                                   20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 7
aacgacgtaa acgaaaatat cg                                                22

<210> SEQ ID NO 8
<211> LENGTH: 1020
<212> TYPE: DNA
<213> ORGANISM: Homo sapiens

<400> SEQUENCE: 8
tttssagttt ttaggtttta tttgtttttt gaataagaaa gaggtttgtt ttggttattt        60
ttttagtttg tttagttttg gtattttgtg agtcggttta ggtagtagtt tcggaataga      120
tgaggtaggt agggttggga cgtttggtta ggatagttta tcgtaaaaag aggaggaaag      180
aaatgaaaga tagagatagt tttggttatg ggagaaggag gaggtcgggg gaaggaggag      240
ataggaggag gagggattac ggggtggagg ggagatagat ttagtttaga gttttgagtg      300
gttttttgtt gtttgttttt aaattttttt atattttcgc ggtttttag attgttcgga       360 gagcgcgttt tgtttgtcgt tgtttgttt gttattgagg tatgtgtgat tttcgtttag       420
tttttttttt ttatagttgt attaatttcg atattttcgt ttacgtcgtt agttcgtgtg      480
taagggaggg aagttttgtt gaggatgcgt ttttttttc ggttttatta cggtttttttt      540 taagagtatg gttttcggtt ttgtttgttt gttgtttttt agaaggtgga tttattgtgt      600 aatttttgttt tttttttatag gtttatagga aaataatttt attatgttttt cgggggagt    660 attttttttat tttttgtttt tttttgtgtt tgttttttggt tttagaggtt gtttgtttgt    720
tttttttgtt tttttttgtaa atgtggtagt ttttttttttt tttgggaatt tgatttttatt  780
```

```
atagttgtta tagggatttg gttagtaatc ggagtttgtt ttttagattt cggttagggg    840
ttttgttttt taaaaaggga ttttgtagaa taattagttg attttttgaaa gggaaagggg    900 gaggttttat tattaattta tatttttggg aagttttgt ttttttttaa tttttttat      960 ttttaaatat tattttcgt ttttttaata tataaatttt agtattattt gtttgaaat     1020
```

<210> SEQ ID NO 9
<211> LENGTH: 360
<212> TYPE: DNA
<213> ORGANISM: Homo sapiens

<400> SEQUENCE: 9

```
ataggaggag gagggattat ggggtggagg ggagatagat ttagtttaga gttttgagtg     60
gttttttgtt gtttgttttt aaattttttt atattttgt ggttttttag attgtttgga    120
gagtgtgttt tgtttgttgt ttgtttgttt gttattgagg tatgtgtgat ttttgtttag   180 ttttttttt ttatagttgt attaattttg atattttgt ttatgttgtt agtttgtgtg    240
taagggaggg aagttttgtt gaggatgtgt tttttttttt ggttttatta tggttttttt   300
taagagtatg gttttggtt ttgtttgttt gttgtttttt agaaggtgga tttattgtgt   360
```

<210> SEQ ID NO 10
<211> LENGTH: 360
<212> TYPE: DNA
<213> ORGANISM: Homo sapiens

<400> SEQUENCE: 10

```
ataggaggag gagggattac ggggtggagg ggagatagat ttagtttaga gttttgagtg     60
gttttttgtt gtttgttttt aaattttttt atattttcgc ggttttttag attgttcgga   120
gagcgcgttt tgtttgtcgt tgtttgttt gttattgagg tatgtgtgat tttcgtttag    180 ttttttttt ttatagttgt attaattcg atattttcgt ttacgtcgtt agttcgtgtg    240
taagggaggg aagttttgtt gaggatgcgt tttttttttc ggttttatta cggttttttt   300
taagagtatg gttttcggtt ttgtttgttt gttgtttttt agaaggtgga tttattgtgt   360
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 11

```
aagatccatg agaatgagaa g                                               21
```

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 12

```
aaaagcgggt ggtgcaatg                                                  19
```

<210> SEQ ID NO 13
<211> LENGTH: 10
<212> TYPE: DNA

```
<213> ORGANISM: Artificial Sequence
<220> FEATURE:
<223> OTHER INFORMATION: Description of Artificial Sequence:
      Synthetic oligonucleotide

<400> SEQUENCE: 13
atgtgaagag                                                                 10

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 14
tttttttttt tttttttttt tttt                                                 24
```